US012527677B2

(12) United States Patent
Fleming

(10) Patent No.: US 12,527,677 B2
(45) Date of Patent: Jan. 20, 2026

(54) CABLE KNEE BRACE SYSTEM

(71) Applicant: MOBIUS TECHNOLOGIES, LLC, Ketchum, ID (US)

(72) Inventor: Darren Fleming, San Diego, CA (US)

(73) Assignee: Mobius Technologies, Inc., Ketchum, ID (US)

( * ) Notice: Subject to any disclaimer, the term of this patent is extended or adjusted under 35 U.S.C. 154(b) by 256 days.

(21) Appl. No.: 17/501,935

(22) Filed: Oct. 14, 2021

(65) Prior Publication Data

US 2022/0257402 A1 Aug. 18, 2022

Related U.S. Application Data

(63) Continuation of application No. 16/436,716, filed on Jun. 10, 2019, now abandoned, which is a continuation-in-part of application No. 13/867,910, filed on Apr. 22, 2013, now Pat. No. 11,123,210, which is a continuation of application No. 12/987,084, filed on Jan. 8, 2011, now abandoned, which is a continuation-in-part of application No. 11/744,213, filed on May 3, 2007, now abandoned.

(60) Provisional application No. 62/718,529, filed on Aug. 14, 2018, provisional application No. 62/682,560, filed on Jun. 8, 2018.

(51) Int. Cl.
*A61F 5/01* (2006.01)

(52) U.S. Cl.
CPC .... *A61F 5/0123* (2013.01); *A61F 2005/0137* (2013.01); *A61F 2005/0167* (2013.01); *A61F 2005/0179* (2013.01)

(58) Field of Classification Search
CPC ...... A61F 5/0123; A61F 5/0125; A61F 5/013; A61F 5/0102; A61F 5/0106; A61F 2005/0132–0176; A61F 2005/0179; A61F 5/01; A61F 5/0127; A61F 5/0193; A61H 1/024
USPC ........... 602/16, 23, 26, 5, 20, 21, 24, 25, 27
See application file for complete search history.

(56) References Cited

U.S. PATENT DOCUMENTS 2,270,685 A * 1/1942 Miller .................. A61F 5/0106 2/24
4,886,054 A * 12/1989 Castillo ................ A61F 5/0123 602/26
4,940,044 A * 7/1990 Castillo ................ A61F 5/0123 623/39
5,131,385 A * 7/1992 Kuehnegger ......... A61F 5/0125 602/26
7,662,122 B2 * 2/2010 Sterling ................ A61F 5/0123 602/61

(Continued)

*Primary Examiner* — Rachael E Bredefeld
*Assistant Examiner* — Seth R. Brown
(74) *Attorney, Agent, or Firm* — Richard T. Black; FisherBroyles, LLP

(57) ABSTRACT

It is the object of the invention to provide a knee bracing system that bolsters the body's natural ligaments, and accommodates user's with different natural Q-angles, to reduce the knees proneness to injury or re-injury. The invention is a cable system that acts much like the body's natural way that resists the forces that cause excessive joint movement and injury to the ACL and or MCL. As the leg travels through the range of motion the cables provide external hyper extension, bending, and rotation support preventing the tibia bone from moving forward (hyper extending) or twisting (lateral rotation) and or laterally bending with respect to the femur.

11 Claims, 17 Drawing Sheets

(56) References Cited

U.S. PATENT DOCUMENTS

| | | | | |
|---|---|---|---|---|
| 2010/0063432 | A1* | 3/2010 | Schimek | A61F 5/0123 602/26 |
| 2011/0098618 | A1* | 4/2011 | Fleming | A61F 5/0123 602/26 |
| 2018/0193180 | A1* | 7/2018 | Bejarano | A61F 5/05858 |

* cited by examiner

CABLE KNEE BRACE SYSTEM

PRIORITY CLAIM

This application claims priority to each of the following applications. This application is a continuation in part of U.S. patent application Ser. No. 13/867,910 filed on Apr. 22, 2013, which is a continuation of U.S. patent application Ser. No. 12/987,084 filed on Jan. 8, 2011, which is a continuation-in-part of U.S. patent application Ser. No. 11/744,213 filed on May 3, 2007. This application also claims priority from U.S. Provisional Application Nos. 62/682,560 filed Jun. 8, 2018 and 62/718,529 filed Aug. 14, 2018.

INCORPORATION BY REFERENCE

The following documents are incorporated by reference in their entirety, U.S. patent application Ser. No. 13/867,910 filed on Apr. 22, 2013, U.S. patent application Ser. No. 12/987,084 filed on Jan. 8, 2011, and U.S. patent application Ser. No. 11/744,213 filed on May 3, 2007.

BACKGROUND OF THE INVENTION

The human knee is a complex mechanism that is highly vulnerable to injury in sports like football, hockey, skiing, snowboarding, and motocross. In these kinds of physically demanding sports the Anterior Cruciate Ligament (ACL) and Medial Collateral Ligaments (MCL) are commonly injured. The ACL controls forward movement of the tibia relative to the femur (hyper extension) and lateral rotation of the tibia with respect to the femur (over rotation). The MCL controls lateral movement of the tibia with respect to the femur. Hyper extending the leg and or laterally rotating or twisting or laterally bending of the leg can tear the ACL and/or MCL. The ACL regulates the amount of movement the tibia has with respect to the femur both in forward movement, and lateral rotation. When the leg reaches full extension the ACL becomes taut and limits the knee from hyper extending or over rotating laterally.

The MCL regulates how much the tibia can bend laterally with respect to the femur. The MCL becomes taut when a lateral force is applied to the leg preventing excessive bending. All too often in sports like motocross the leg is exposed to forces that exceed the ligament's ability to prevent excessive movement in the joint sometimes resulting in the tearing of the ACL and or MCL.

In order for a knee brace to be effective in resisting the excessive movement of the knee joint that tears the ACL and/or MCL, it must provide an effective differential force to the tibia relative to the femur. Because of the large amount of flesh surrounding the tibia bone and femur bone the only way to prevent the leg from over extending or over rotating would be to fix a rigid structure to the bones with some sort of mechanical means such as screws. Of course this would be impractical and undesirable. Not only should a knee brace be practical, it must be comfortable, and most of all effective at preventing knee injuries.

Most prior art (conventional) knee brace devices for ligament protection consist of a rigid femoral plate and tibial plate connected by hinges on either side of the knee. The plates are strapped to the leg tightly above and below the knee with straps that encircle the leg. The hinge locks as the leg reaches full extension and the rigid frame and straps act like a splint resisting hyperextension of the leg. There are many variations of the basic rigid hinged brace with differing hinge designs, strapping methods, and materials used.

Conventional braces are limited in their effectiveness resisting excessive joint movement that causes injury to the knee. The biggest reason is that the flesh of the leg surrounding the femur and the strapping apparatus deform allowing the leg to hyperextend or rotate. Even when the strapping devices are tightened to the point of discomfort, they have limited effect preventing excessive movement of the knee joint when the leg is subjected to these forces.

It is the object of the invention to provide a knee bracing system that bolsters the body's natural ligaments to reduce the knees proneness to injury or re-injury.

The invention is a cable system that acts much like the body's natural ACL and MCL. The cables are routed around the knee joint in a way that resists the forces that cause excessive joint movement and injury to the ACL and or MCL. As the leg travels through the range of motion the cables tighten, preventing the tibia bone from moving forward (hyperextending) or twisting (lateral rotation) or bending laterally with respect to the femur.

The cable knee brace system of this invention can be tailored or adapted to prior art (conventional) braces increasing their effectiveness.

It is also anticipated by the Applicant that this cable knee brace system can be adapted to the elbow to prevent the arm from hyperextending. A humorous plate would substitute for the femoral plate 4, a radius plate would substitute for the tibial plate 2, and bicep plate would substitute for the femoral back plate 5 creating the differential resistive force across the elbow joint preventing hyperextension of the arm.

DETAILED DESCRIPTION

Figure 1:
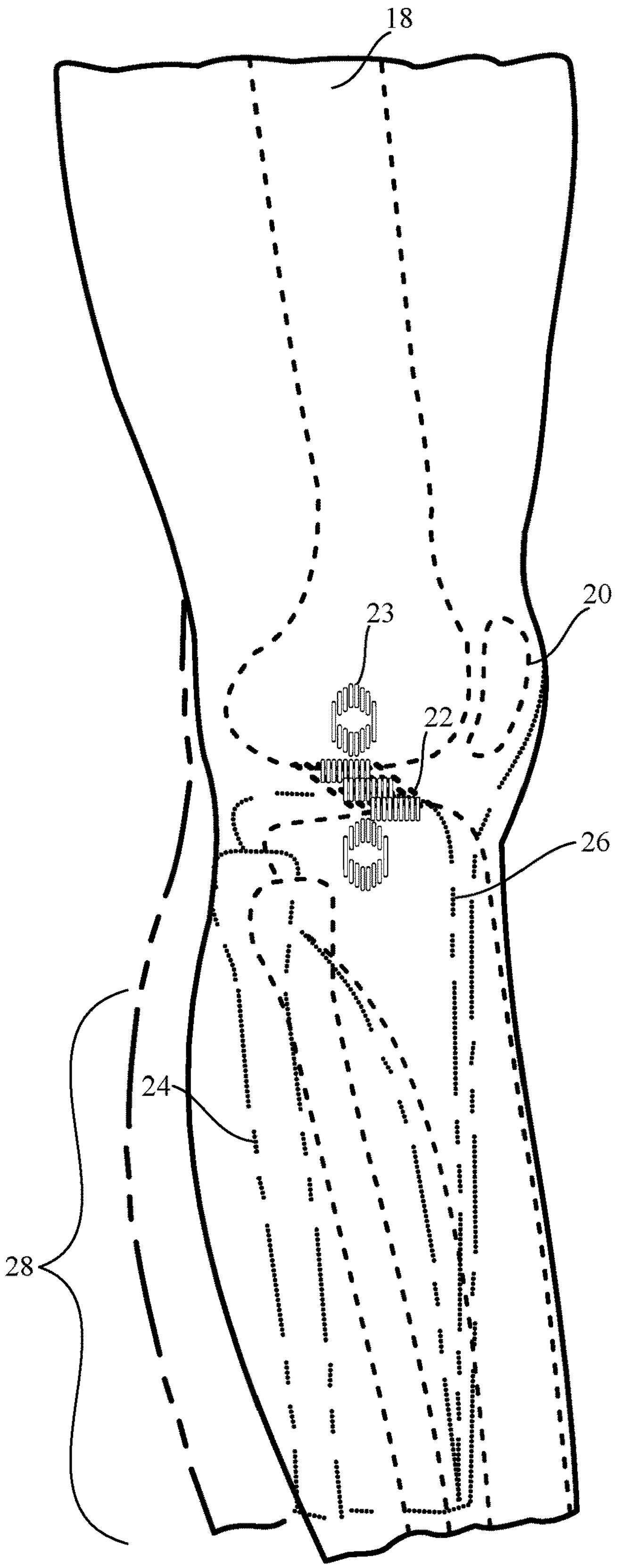
FIG. 1 is an outside elevation/side view of a right leg showing normal fully extended and hyperextended (tearing ACL) views.
Figure 2:
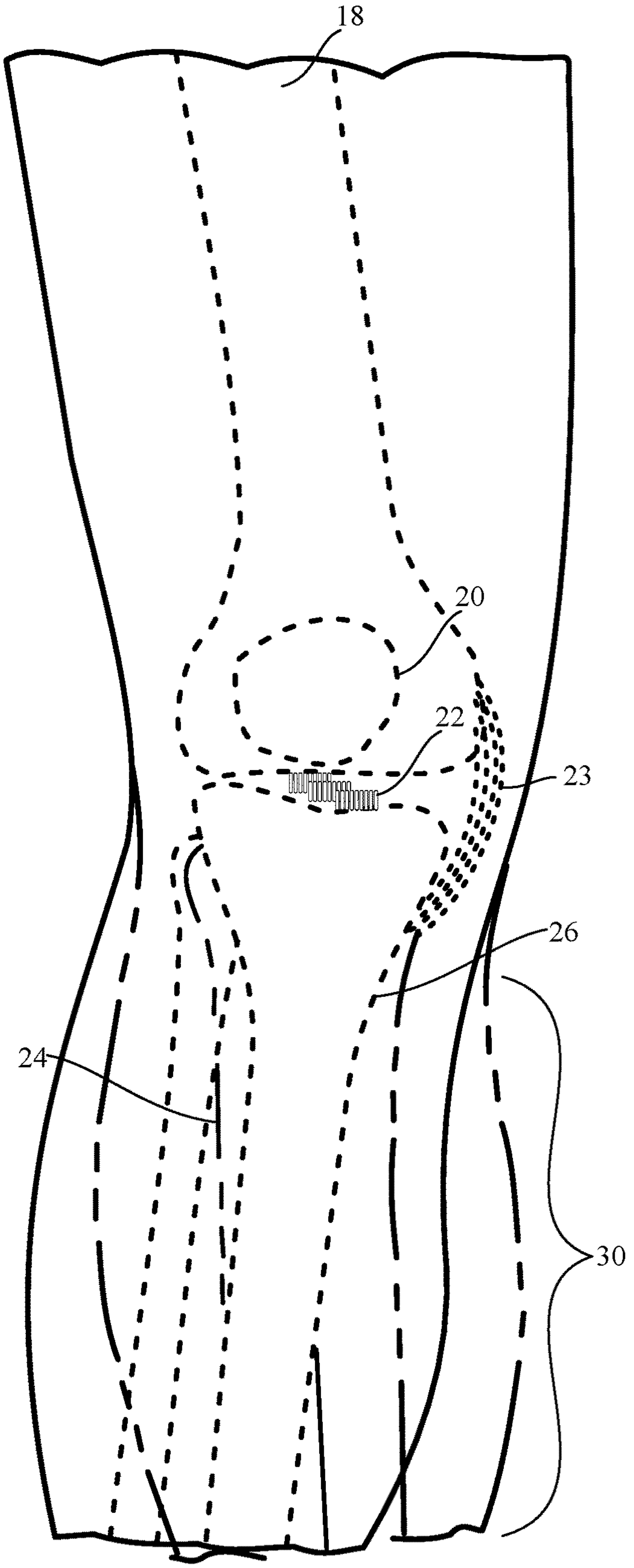
FIG. 2 is a top/front view of the right leg fully extended showing normal and laterally rotated or laterally bent (tearing ACL and or MCL) views.

To be effective preventing injuries to the ACL 22 and or MCL 23, a knee brace must prevent the tibia bone 26 from moving forward (hyperextending), see FIG. 1, or laterally bending and or rotating (twisting), see FIG. 2, with respect to the femur bone 18. The patella 20 and fibula bone 24 are shown for completeness. The knee brace of this invention as best shown in FIGS. 3-17, which like references refer to like elements throughout the several views, introduces a novel cable system that more effectively prevents hyperextension, lateral bending and or lateral rotation of the knee joint.

Figure 3:
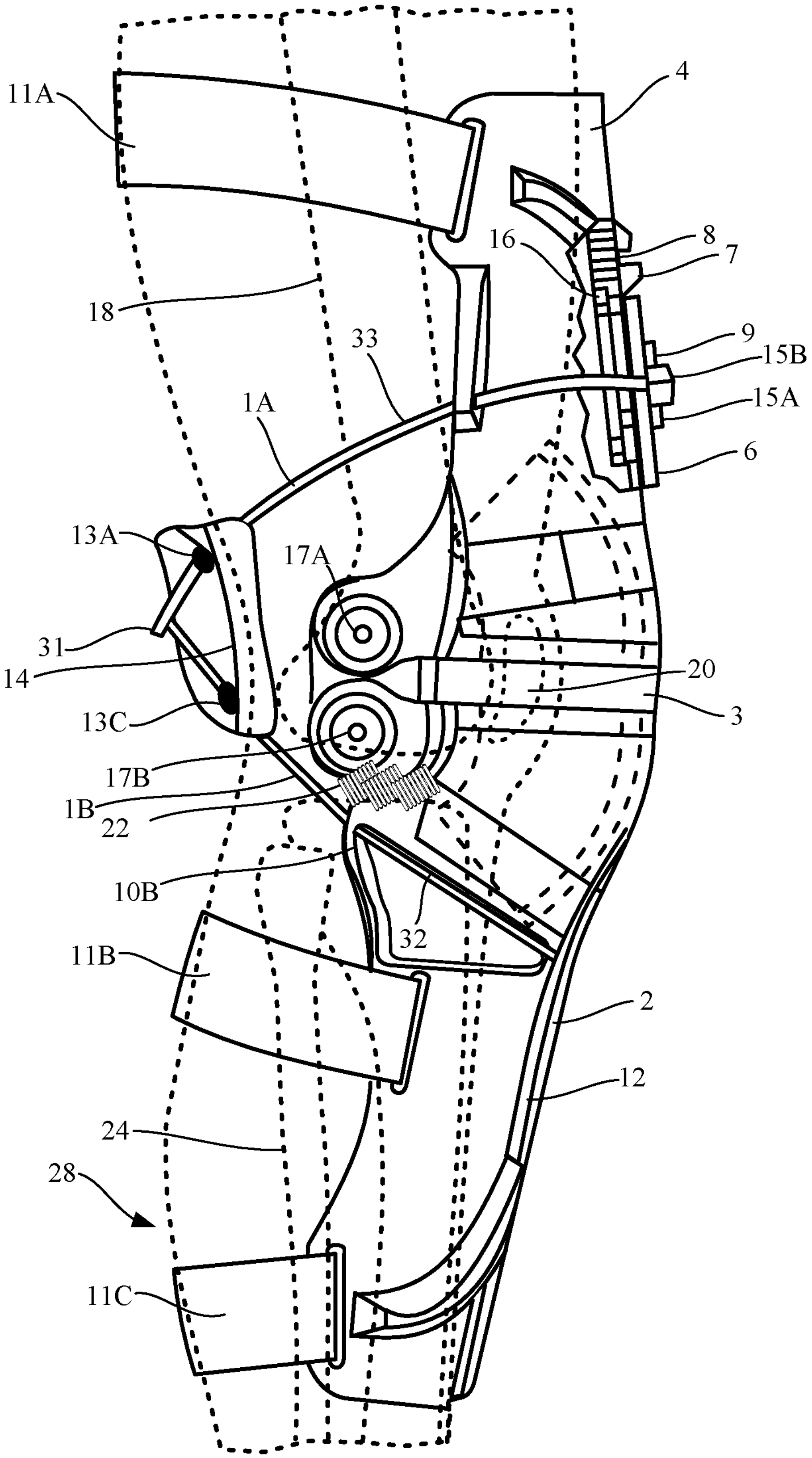
FIG. 3 is an outside elevation/side view of the right leg fully extended showing the primary cable resisting hyperextension of the leg.
Figure 4:
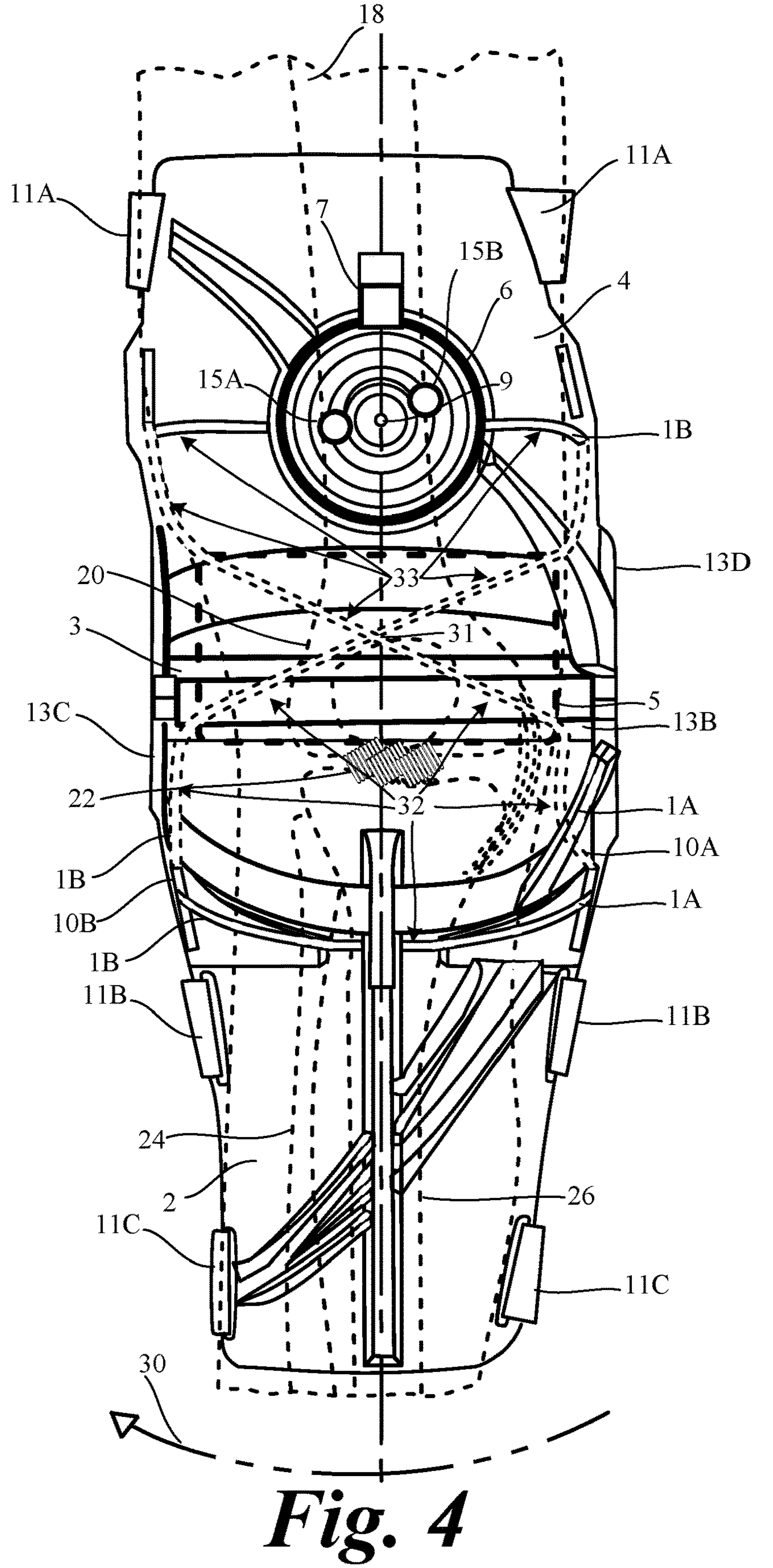
FIG. 4 is a top/front view of the right leg fully extended showing the primary cable resisting lateral rotation of the leg.
Figure 5:
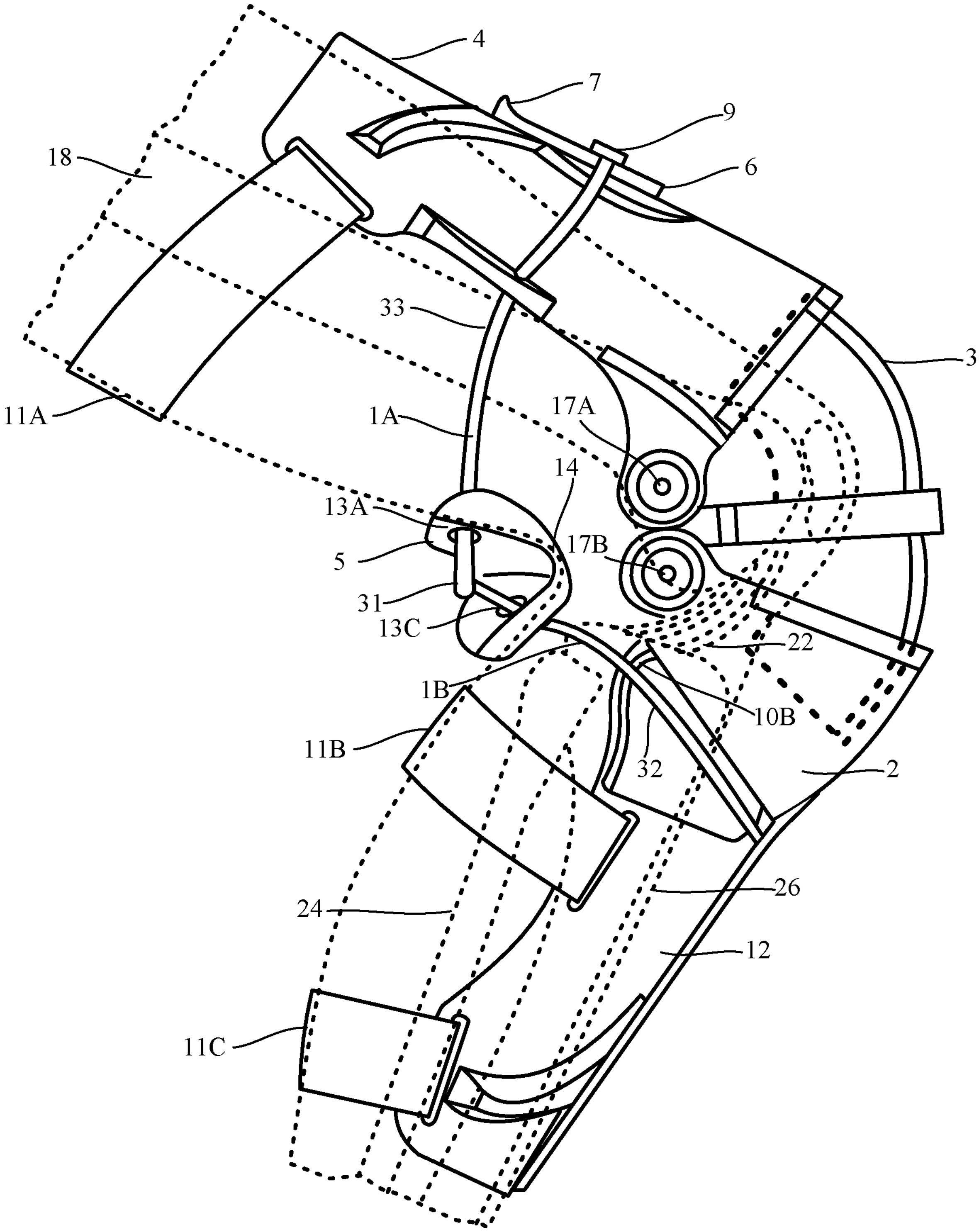
FIG. 5 is an outside elevation/side view of the right leg in the flexed position showing the primary cable knee brace system.
Figure 7:
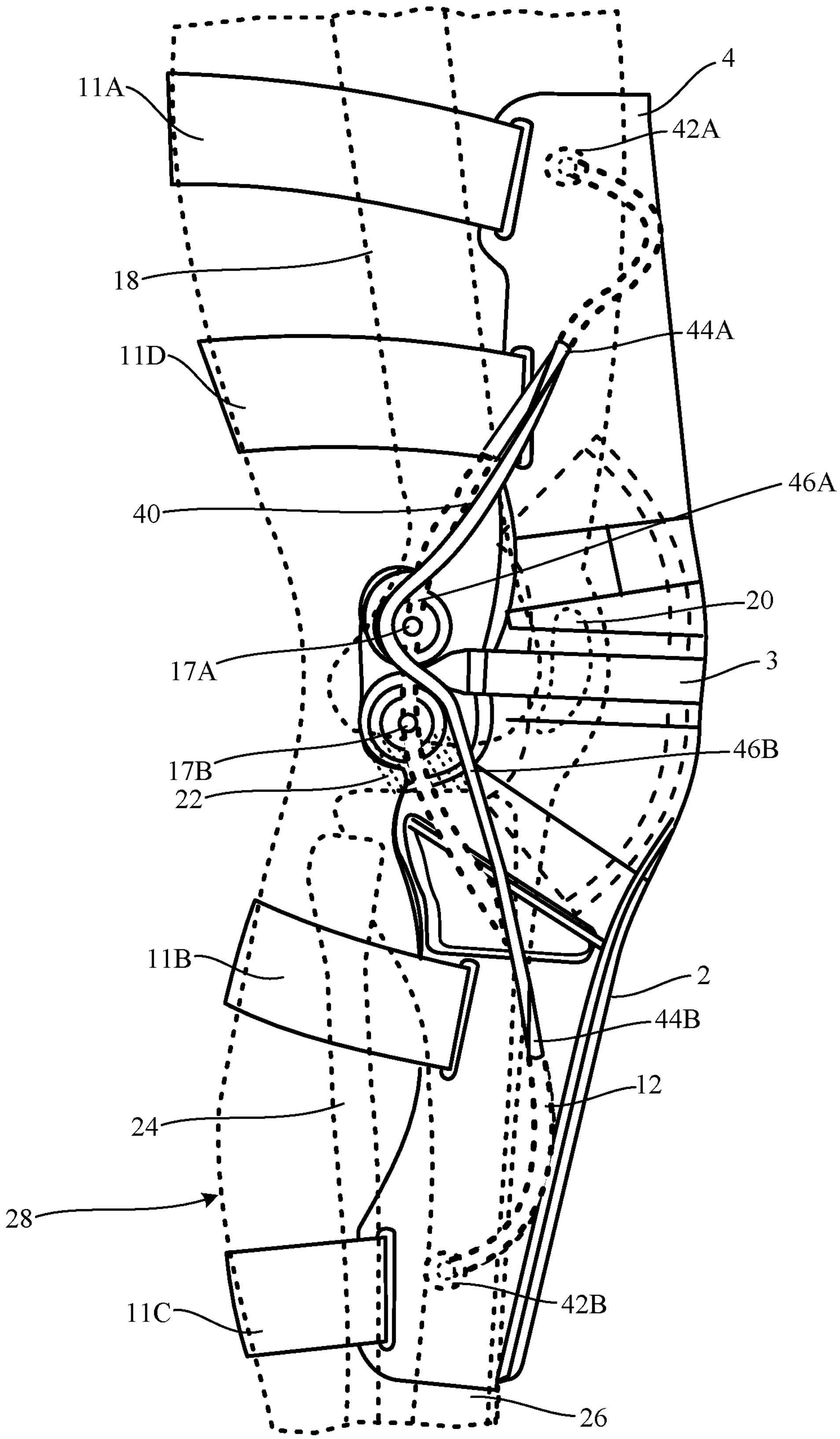
FIG. 7 is an outside elevation/side view of the left leg fully extended showing the secondary cable resisting hyper extension of the leg.
Figure 8:
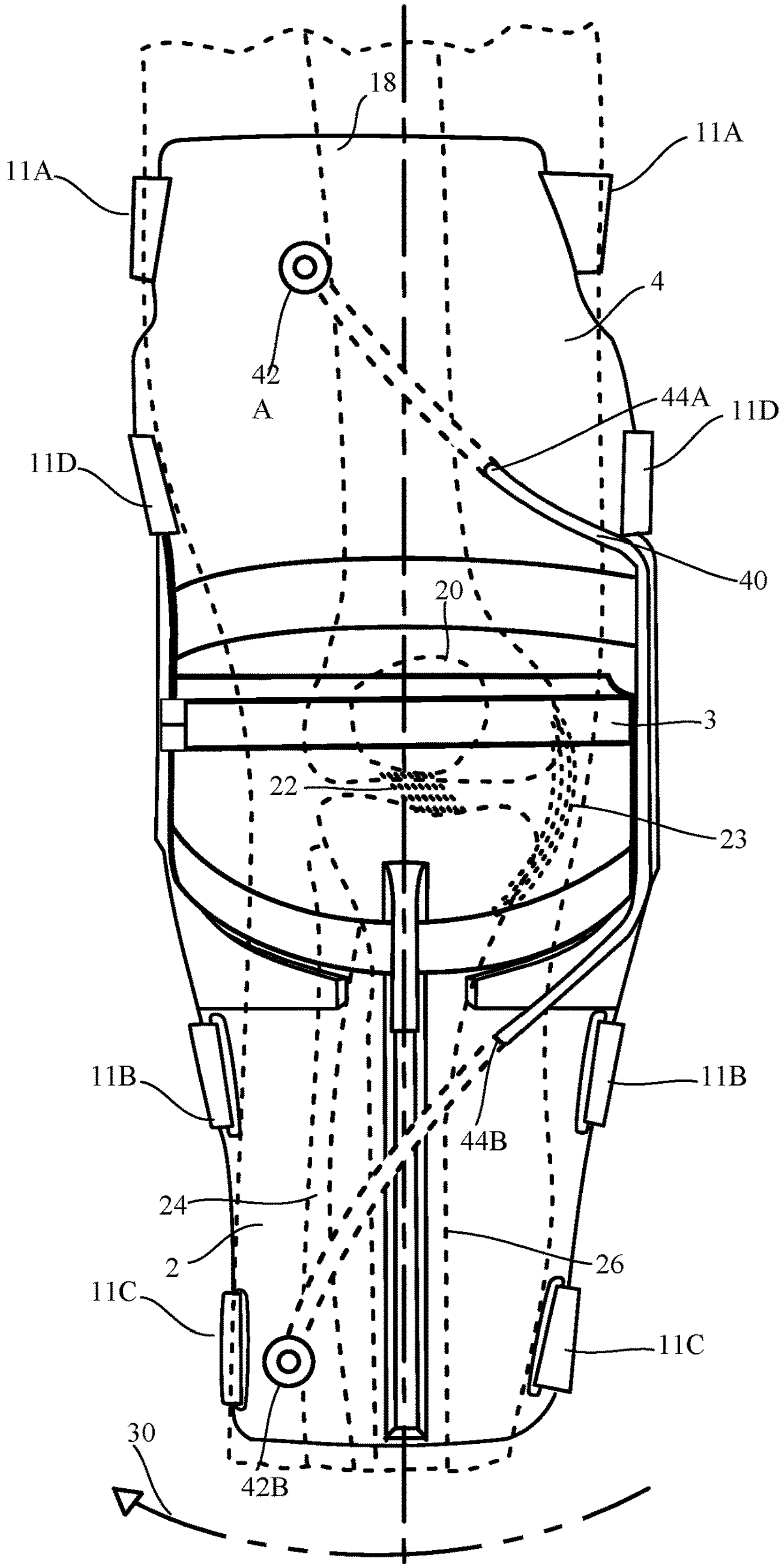
FIG. 8 is a top/front view of the right leg fully extended showing the secondary cable resisting lateral rotation and or lateral bending of the leg.
Figure 9:
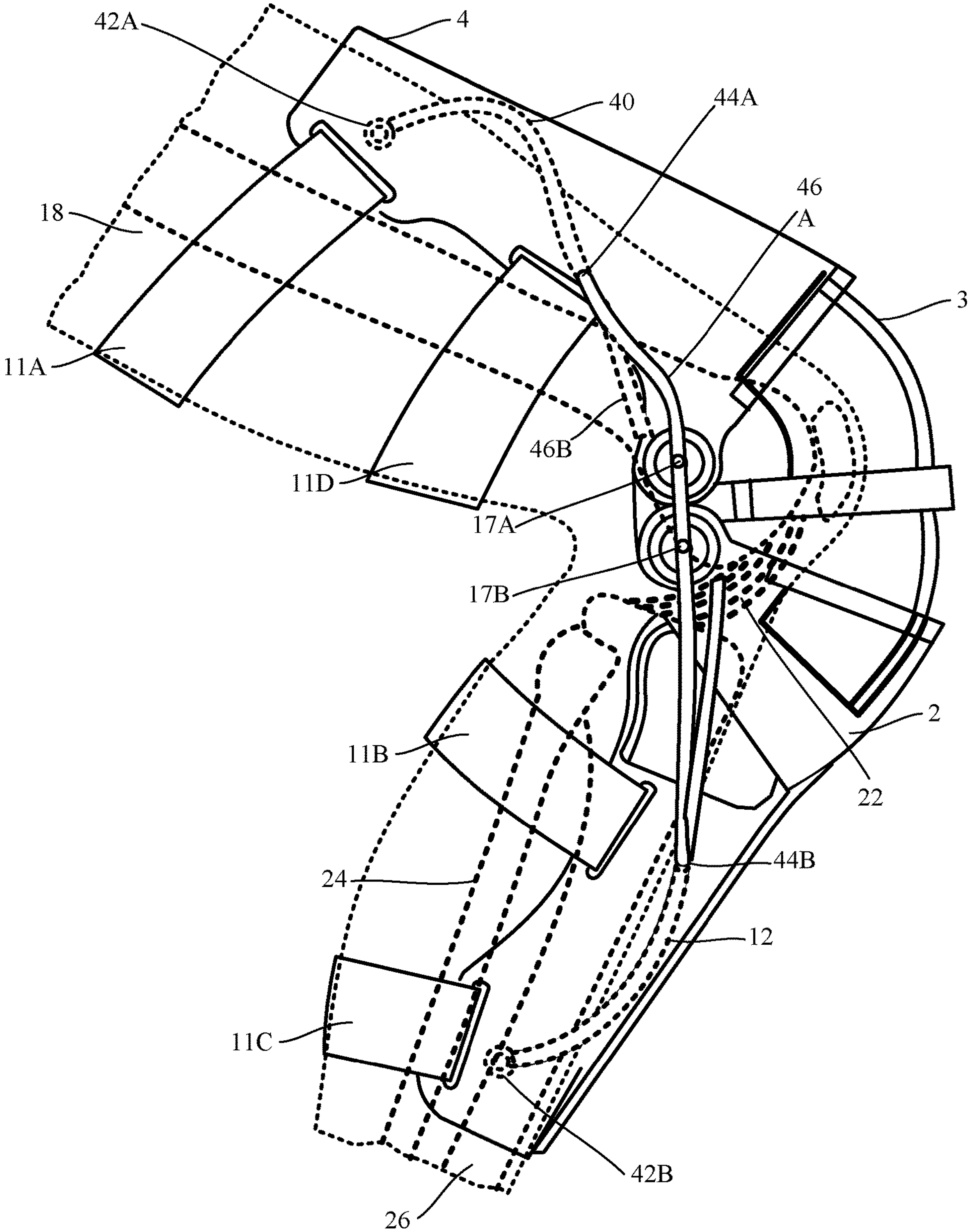
FIG. 9 is an outside elevation/side view of the left leg in the flexed position showing the secondary cable resisting lateral bending or lateral rotation.

FIG. 3 shows the primary cable system of this invention creating an effective differential force to the tibia 26 relative to the femur 18 and reinforcing the ACL 22. When the primary cable 1 of this system is properly tensioned, the brace acts like the body's own ACL 22 becoming taut as the leg extends resisting the forward movement of the tibia bone 26, with respect to the femur bone 18. FIG. 4 shows the primary cable system of this invention resisting the lateral rotation of the tibia bone 26, with respect to the femur bone 18. FIG. 5 shows the primary cable system of this invention when the leg is flexed. As shown in FIG. 3, because the tibial plate 2 moves further away from the femoral plate 4 as the leg extends, the primary cable 1 becomes progressively tighter as the leg approaches full extension. When a hyperextension force 28 is applied to the leg as shown in FIG. 3, the tibial plate 2, patellar plate 3, and femoral plate 4 are compressed together as the primary cable 1 comes under progressively more tension. The tensile force in the primary cable 1 pulls down on the tibial plate 2, and up on the back plate 5, creating the differential resistive force across the knee joint preventing hyperextension of the leg. FIG. 7 shows the secondary cable system of this invention creating an effective differential force to the tibia 26 relative to the femur 18, and reinforcing the ACL 22 and MCL 23. As the leg extends the secondary cable 40 resists the forward movement of the tibia bone 26, with respect to the femur bone 18. FIG. 8, shows the secondary cable 40 resisting the lateral bending and or lateral rotation of the tibia bone 26, with respect to the femur bone 18. FIG. 9 shows the secondary cable system of the invention when the leg is flexed and the secondary cable 40 resisting lateral bending and lateral rotation throughout the leg's range of motion. As the leg extends the patellar plate 3 acts like a hinge for the tibial plate 2 and femoral plate 4, rotating about pivot points 17*a* and 17*b*, respectively, approximating the knees flexion-extension movement.

When a lateral rotation force 30 is applied to the leg as shown in FIG. 4 the tibial plate 2, patellar plate 3, femoral plate 4, and back plate 5 are held rigid by the tension developed in the primary cable 1. The tensile forces in primary cable 1 cross behind the leg, creating cable cross over point 31 as they pass through back plate 5, resisting rotation and bending across the knee joint and preventing the leg from laterally bending or rotating. When a lateral bending or lateral rotation force is applied to the leg as shown in FIG. 8, the tibial plate 2, patellar plate 3, and femoral plate 4 are held rigid by the tension developed in the secondary cable 40. The tension in the secondary cable 40 prevents the brace from bending across the knee joint preventing the leg from laterally bending or rotating.

This invention comprises of a primary cable 1 and secondary cable 40 that can be made of any flexible material with a sufficiently high tensile strength. A tibial plate 2 that could be made of any rigid or semi-rigid material is shaped to conform to the tibia bone 26, beginning just below the knee and ending approximately at the midpoint of the tibia bone 26. The tibial plate 2 is held in position with straps 11*b* and 11*c*. Foam padding 12 is attached to the underside of the tibial plate 2 for comfort and to provide a firm grip on the individuals' tibia bone 26. A patellar plate 3 that could be made of any rigid or semi-rigid material connects the tibial plate 2 to the femoral plate 4. A femoral plate 4 that could be made of any rigid or semi-rigid material is located on top of the thigh from just above the knee to approximately mid-femur 18 and is held in position with strap 11*a*. Back plate 5 could be made of any rigid or semi-rigid material located behind the leg and just above the knee joint to keep the cable 1 in the proper location, firmly holding the femur bone 18 as the differential force of the primary cable 1 is transmitted across the joint. Foam padding 14 is attached to the inside of the back plate 5 to help spread the force of the primary cable 1 comfortably to the leg. A cable tensioner dial 6 and locking/release button 7 with spring 8 are attached to the femoral plate 4 with retainer screw 9. These could be made from any metal or rigid material that will withstand the forces required to keep the primary cable 1 locked in place during use. Other cable tensioning and locking mechanisms could be used, but the dial tensioning and locking system gives a very wide range of fine tuned cable adjustability and ease of use.

Figure 6:
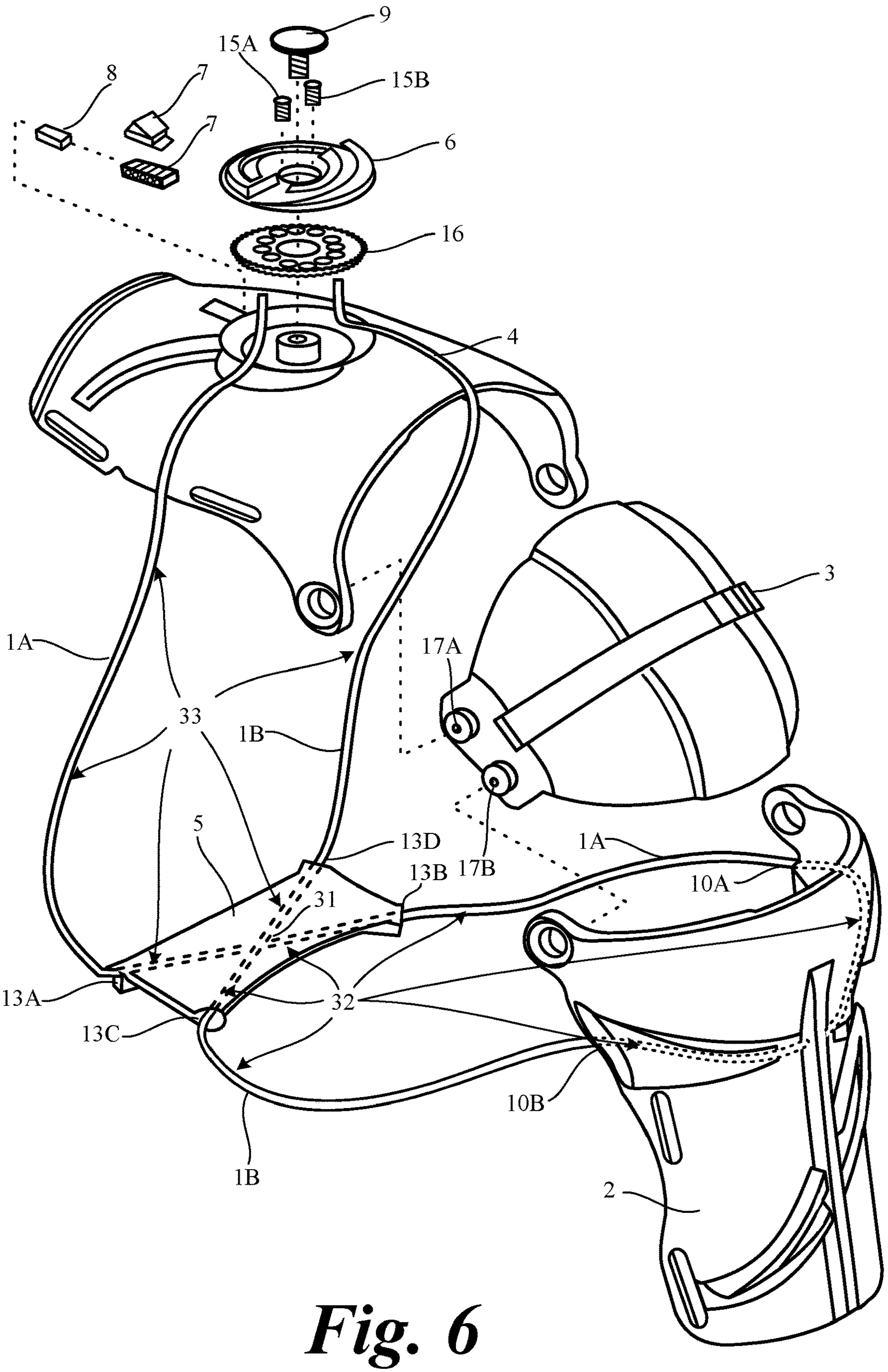
FIG. 6 is an exploded isometric view showing the individual parts of the primary cable knee brace system.

The fundamental element of this invention is the routing of the cables. As best shown in FIG. 6, primary cable 1 begins attached to femoral plate 4 by cable connector 15*a*, crosses behind the leg through cable guide hole 13*a* and cable guide hole 13*b* in back plate 5, and runs through a cable guide hole on the opposite side of tibial plate 2. The primary cable 1 then loops over the leg through a cable guide hole and through the cable guide hole to the other side of tibial plate 2. From the cable guide hole in tibial plate 2, the primary cable 1 again crosses behind the leg through cable guide hole 13*c*, crossing over itself, creating cable cross over point 31, before going through cable guide hole 13*d* in back plate 5, and attaches to the opposite side of femoral plate 4 by second cable connector 15*b*.

In additional embodiments, primary cable 1 begins attached to femoral plate 4 by first cable connector 15*a*, crosses behind the leg through first cable guide hole 13*a* and second cable guide hole 13*b* in back plate 5, creating cable cross over point 31, and attaches to the opposite side of tibial plate 2 with clamping screw 10*a*. The primary cable 1 then loops over the leg attaching to the other side of tibial plate 2 with clamping screw 10*b*. From clamping screw 10*b*, the primary cable 1 again crosses behind the leg through third cable guide hole 13*c* and fourth cable guide hole 13*d* in back plate 5, and attaches to the opposite side of femoral plate 4 by the second cable connector 15*b*.

Figure 10:
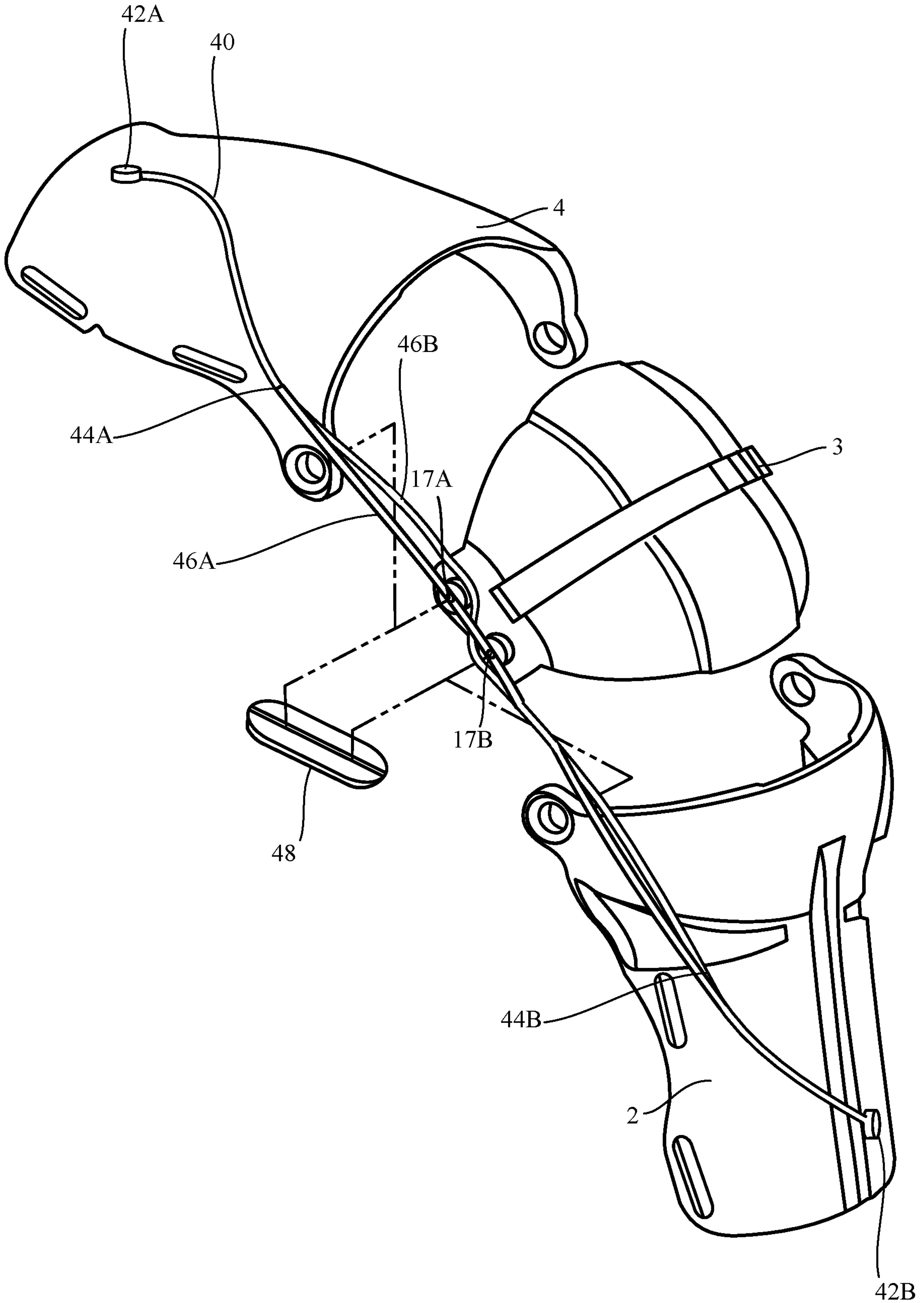
FIG. 10 is an exploded isometric view of the individual parts of the secondary cable knee brace system.

As best shown in FIG. 10, secondary cable 40 begins attached to the outside, or collateral side, of the femoral plate 4 by the femoral cable connector 42*a* and runs through the femoral cable guide hole 44*a*. The secondary cable 40 crosses femoral pivot point 17*a* and tibial pivot point 17*b* through cable guide plate 48. From there, the secondary cable 40 runs through tibial plate guide hole 44*b* and attaches to the outside, or lateral side, of the tibial plate 2 by the tibial cable connector 42*b*, completing the route.

In some embodiments, a single cable is used as it passes through the various guides. In alternative embodiments, the cable could be made up of individual segments connected together to form the completed routing. For example, first primary cable segment 1*a* and second primary cable segment 1*b* can be formed by a single cable, or can be two separate cables connected together with tibial plate 2 to complete the loop. First primary cable segment 1*a* begins attached to femoral plate 4 by first cable connector 15*a*, crosses behind the leg through the cable guide hole 13*a* and cable guide hole 13*b* in back plate 5 and attaches to the opposite side of tibial plate 2 with clamping screw 10*a*. Without having to loop over the leg, the second primary cable segment 1*b* is attached to the opposite side of tibial plate 2 with clamping screw 10*b*. From clamping screw 10*b* the second primary cable segment 1*b* crosses behind the leg through the cable guide hole 13*c*, and crossing over itself, creating cross over point 31, before going through cable guide hole 13*d* in back plate 5 and completes the loop by attaching to the opposite side of femoral plate 4 with cable connector 15*b*.

The segments of the cable extending from the cable cross over point 31 to the tibial plate portion of the brace and returning to the cable cross over point 31 form the tibial control loop portion 32 of the cable. The segments of cable extending from the cable cross over point 31 to the femoral plate portion of the brace and returning to the cable cross over point 31 form the femoral control loop portion 33 of the cable. FIG. 6, for example, illustrates these control loop portions 32 and 33. During use, for example when the knee is extended toward hyperextension, the tibial control loop will lengthen, causing an inverse tightening of the femoral control loop.

The primary cable 1 is adjusted by turning the cable tensioner dial 6 taking up the excess primary cable 1 length. The primary cable 1 is automatically locked into place by the ratcheting gears 16 on the cable tensioning dial 6 and spring 8 actuated locking/release button 7. The button 7 is also used to release the tension in primary cable 1 for installation and removal of the brace.

Figure 11:
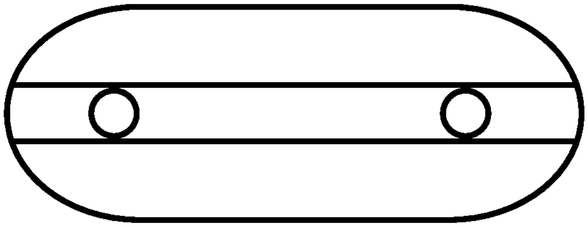
FIG. 11 is an inside elevation/side view of the secondary cable guide plate that guides the secondary cable through the pivot points.
Figure 12:
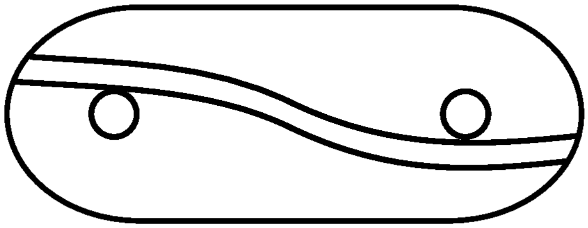
FIG. 12 is an inside elevation/side view of an alternate cable guide plate that guides the secondary cable under and over the pivot points.
Figure 13:
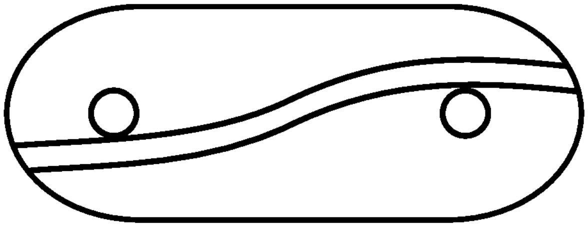
FIG. 13 is an inside elevation/side view of another alternative cable guide plate that guides the secondary cable over and under the pivot points.

While an infinite number of secondary cable routings across the pivot points are possible, directly through the pivot points as shown in 46*a* is most desirable to achieve optimum tension on the secondary cable 40 throughout the leg's full range of motion. FIG. 11 shows a cable guide plate which guides the cable directly through the pivot points, secondary cable routing 46*a*, as described above. Alternate secondary cable guide plate configurations as shown in FIGS. 12 and 13 could be used guide the secondary cable around the pivot points. For example, alternate secondary cable routing 46*b* could be achieved using the cable guide plate shown in FIG. 13 which guides the secondary cable 40 over, or to the fore of, femoral pivot point 17*a* and under, or to the aft of, tibial pivot point 17*b*.

Figure 14:
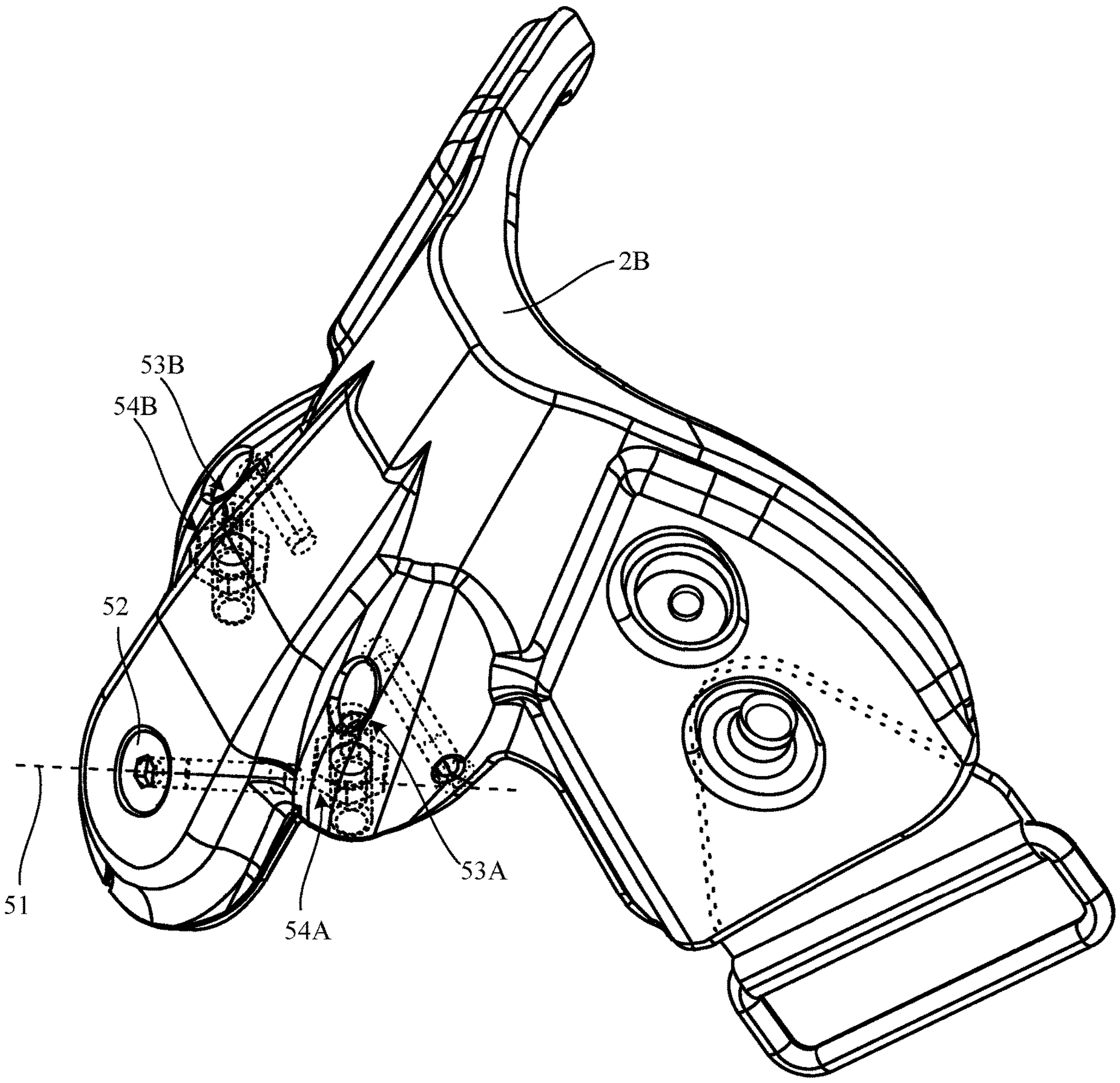
FIG. 14 is a top view of a portion of a Q-adjustable tibial shell according to an embodiment of the present invention.
Figure 15:
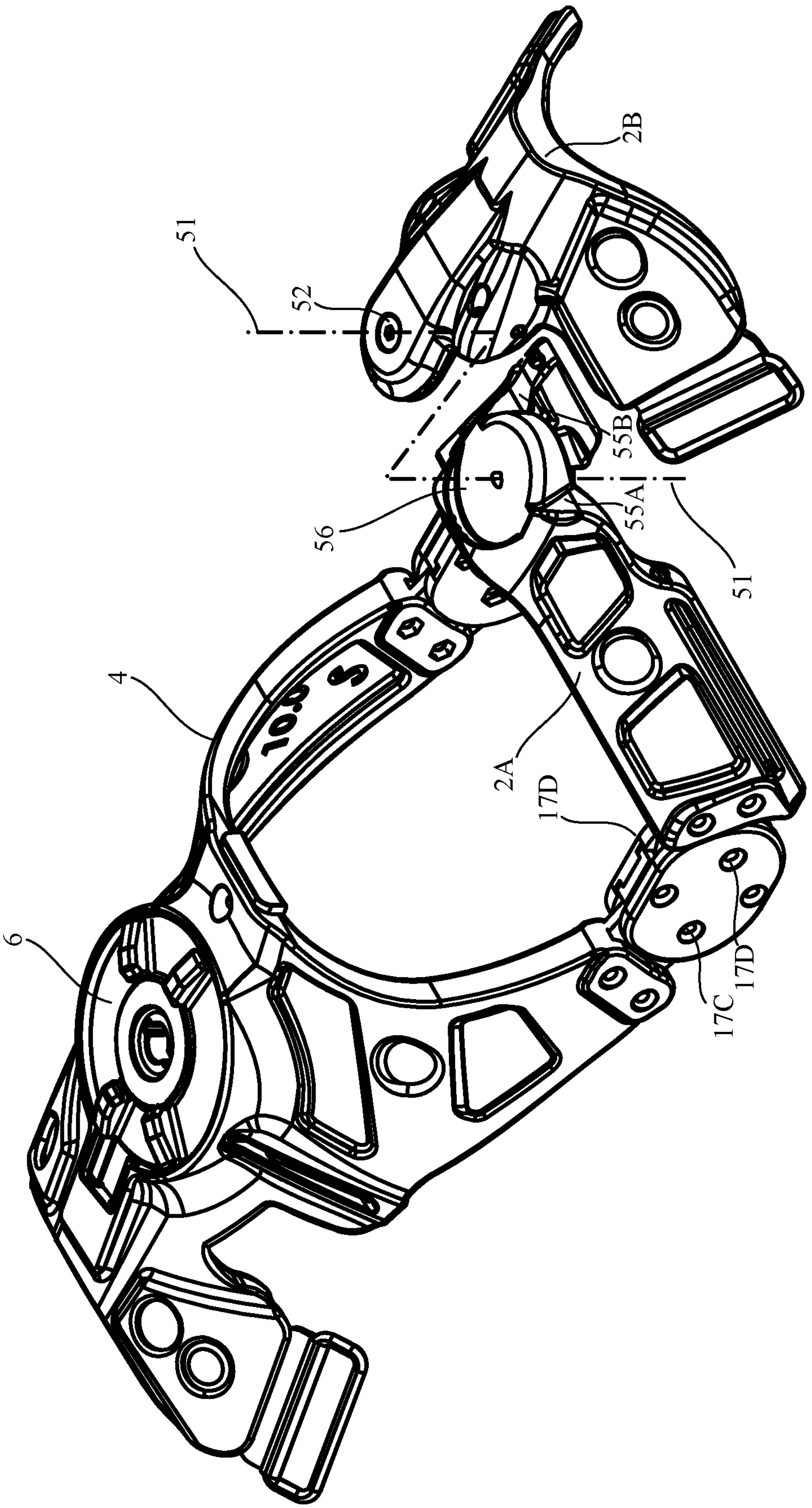
FIG. 15 is a three-quarter view of a Q-adjustable leg brace according to an embodiment of the present invention.
Figure 16:
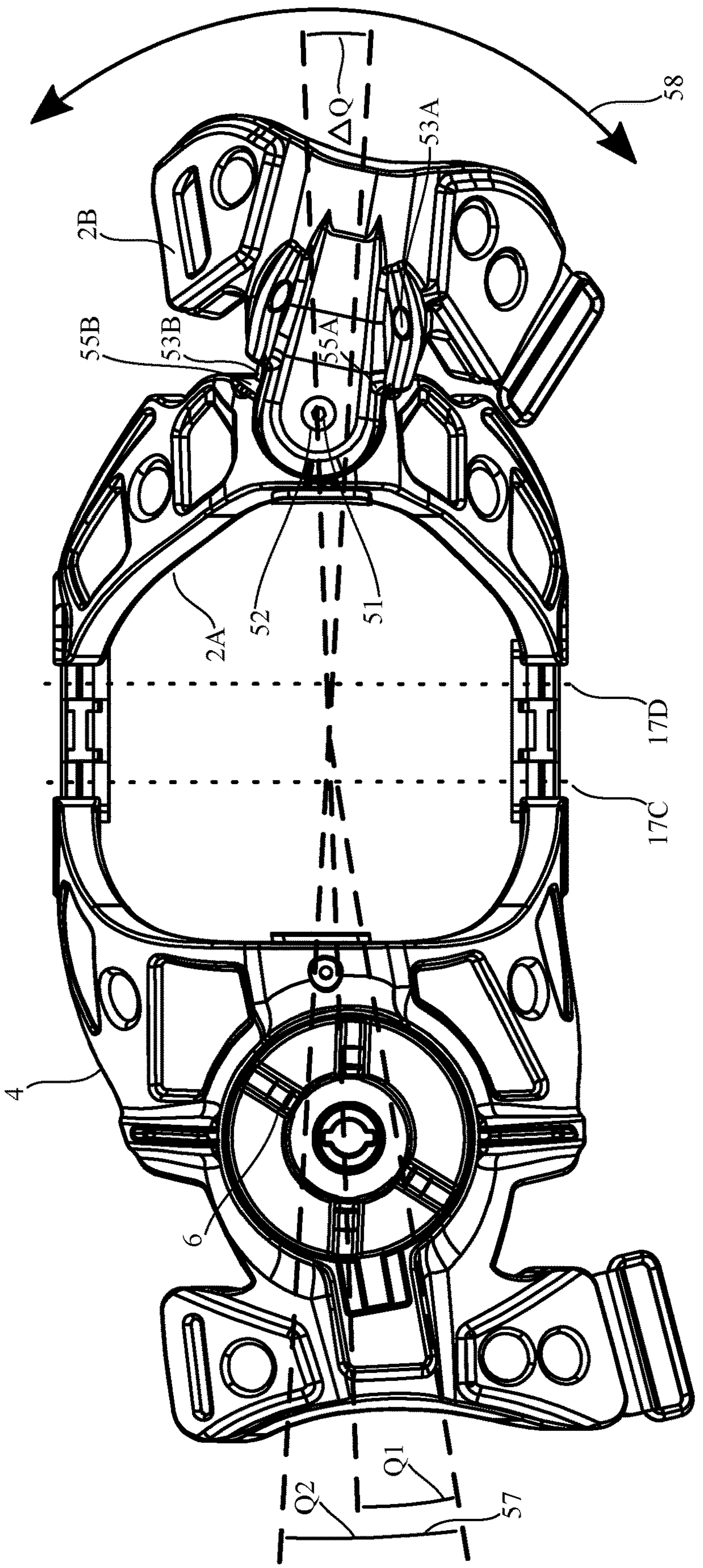
FIG. 16 is a top down view of a Q-adjustable leg brace according to an embodiment of the present invention.

FIG. 15 depicts an alternative tibial shell arrangement. When configured in this manner, the tibial shell 2B mounts to the tibial shell 2A at point 51, forming the axis of rotation. The shell 2B is secured to the tibial shell 2A using tibial adjustment locking screw 52. The tibial shell 2B rotates about axis 51 in order to establish the desired Q-angle, as depicted in FIG. 16. The relative rotation of the tibial shell 2B about axis 51 is controlled using screws 53A-B on either side of the tibial shell 2B, as depicted in FIG. 14. By lengthening or shortening the adjustment screws, which push against corresponding bearing surface 55A-B, the tibial shell pivots accordingly about the axis 51.

FIG. 14 best depicts the adjustment mechanism showing adjustment screws 53A-B threaded through retention nuts 54A-B in tibial shell 2B. As best shown in FIG. 16, after loosening adjustment locking screw 52 and then shortening adjustment screw 53A, lengthening adjustment screw 53B pushes against bearing surface 55B on tibial shell 2A, forcing tibial shell 2B to rotate clockwise about axis 51 until adjustment screw 53A contacts bearing surface 55A on tibial shell 2A before tightening adjustment locking screw 52.

Cable guides accept the cable, the cable being comprised of one or more segments, which transfers energy to control knee movement and prevent hyperextension of the knee joint in the same manner as the other embodiments described above, for example, FIGS. 2-6. In the same manner as the embodiments described above, the cable may be composed of one or multiple portions. While the routing of the cable is not depicted, in a preferred embodiment, the cable beginning from cross over point 31, extends to a first side of tibial shell 2A passing through one or more cable guide holes, then extends over tibial shell 2B through one or more cable guide holes, and then extends back down the opposite side of tibial shell 2A through one or more cable guide holes and then extends back to cable cross over point 31, forming the tibial control loop 32.

When the knee of the user extends, the cable portion extending from a cross over point 31 around the tibial shell 2B and returning to the cross over point, the tibial control loop 32, lengthens accordingly. This produces a direct response in the portion of the cable which extends from the cross over point 31 over and around the femoral plate, the femoral control loop. That portion of the cable tightens, bringing the femoral plate and the back plate 5 into the leg and behind the knee joint respectively, and stopping further extension of the knee by controlling the length of the tibial control loop, FIG. 15 depicts both the femoral shell 4 and tibial shells 2A and 2B of a knee brace according to an embodiment of the present invention. Notably, the back plate, straps, and cable routing are absent in order to more clearly depict the arrangement of the adjustable tibial shell 2B. As depicted, the invention according to this alternative embodiment maintains many of the features described in alternative embodiments herein, including: 4, 6, 17C and 17D. FIG. 15 depicts the tibial shell 2B of FIG. 14 as well as its mounting surface 56 on tibial shell 2A. The axis of rotation 51 is clearly depicted as running through the point at which the tibial shells 2A-B are connected.

Foam padding may be strategically placed at various points on the inside portions of the brace depicted in FIG. 15. For example, on the sides near hinge point 17C and 17D, and underneath tibial shells 2A and 2B as well as femoral shell 4. This foam provides increased comfort to the user.

FIG. 16 depicts the adjustability of the tibial shell 2B which creates a chosen Q-angle 57. The angle between the tibia and the femur forms the quadriceps angle, herein referred to as the Q-angle 57. This angle varies depending on the physiology of the user. The tibial shell 2B is adjustable in order to customize the Q-angle 57 to accommodate each user. By turning the adjustment screws 53A-B, the Q-angle 57 may be changed as the tibial shell 2B pivots 58. The Q-angle is adjustable in either direction. In preferred embodiments, the Q-angle 57 is adjustable up to 4 degrees in either direction, ΔQ. A Q-angle of less than average, is defined as Varus. In this embodiment, the Q-angle 57 may be referred to as negative, for example, the brace may be adjusted −4 degrees from average, ΔQ, forming a more acute Q-angle 57. A Q-angle greater than normal is referred to as Valgus, and may be formed by adjusting the brace to increase the Q-angle, for example +4 degrees from average. The depicted arrangement in FIG. 16 shows, for example, a Valgus arrangement, where the Q-angle of the brace, Q2, is greater than an average angle, Q1. In order to achieve this, the tibial plate 2B has been adjusted toward the outside of the user's leg (right side knee brace). Once the user is happy with their customized Q-angle, they can lock the brace using locking screw 52. This prevents the Q-angle from changing while the user is wearing the device.

Figure 17:
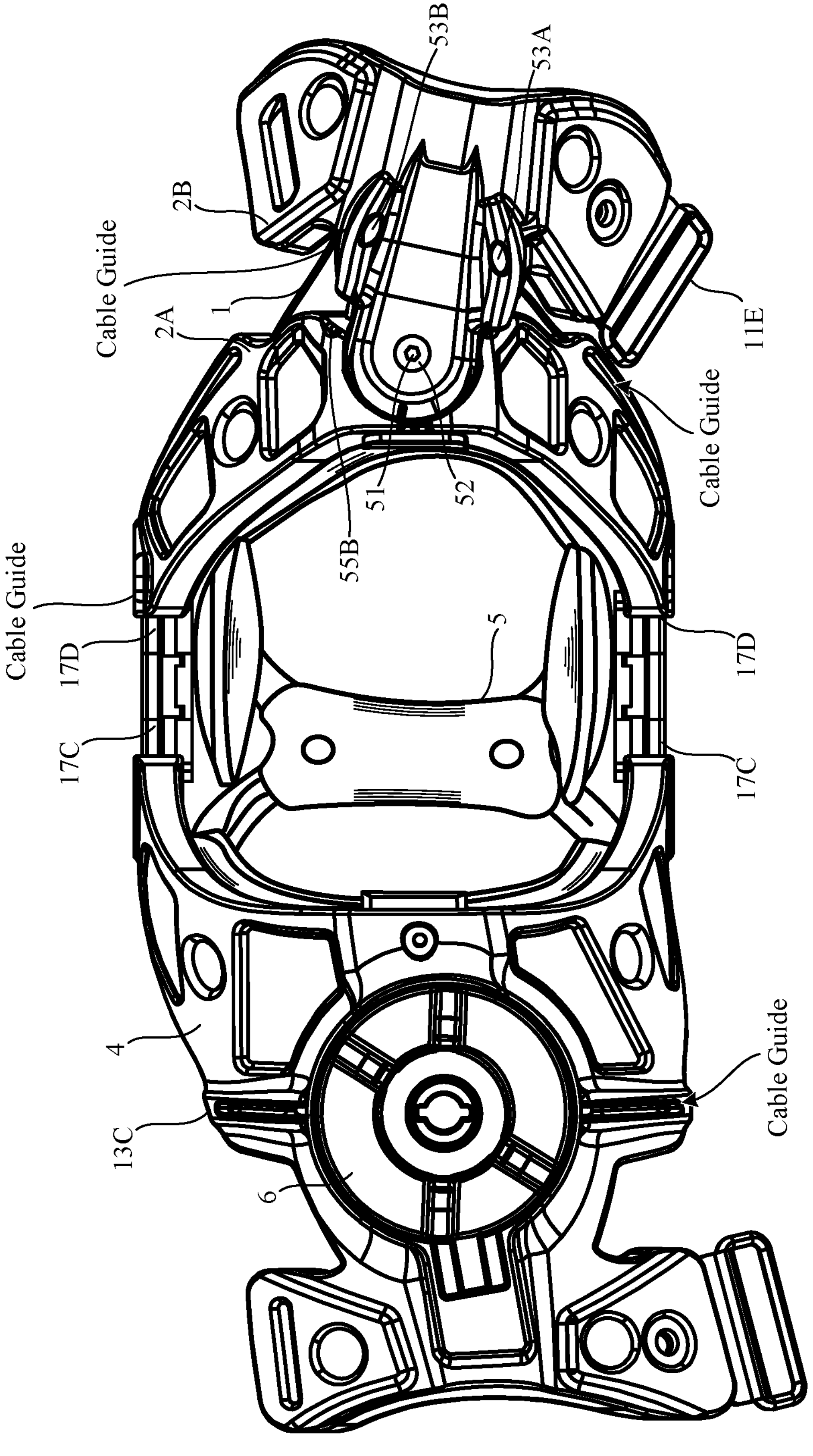
FIG. 17 is a top down view of a Q-adjustable leg brace according to an embodiment of the present invention.

FIG. 17 depicts an embodiment of the present invention with the femoral back plate 5 installed. As depicted, the back plate is positioned just above the knee joint, behind the user's knee. The back plate 5 guides the portions of the cable 1 to a cross over point 31, not shown, located on its back side. Each portion of the cable 1, is then guided back up toward the upper portion of the brace, for example to either side of the femoral plate 4, and the first tibial plate 2A. Cable guide holes along the perimeter of tibial plate 2A are also shown, these guide holes receive the cable from the femoral back plate 5, and guide the cable 1 along tibial plate 2A toward and to tibial plate 2B where the cable 1 enters another guide hole in tibial plate 2B before crossing over to the other side of tibial plate 2B and returning along the same path on the opposite side of the brace. This portion of the cable's path, from the cross over point 31 to the tibial plate 2B and back forming the tibial control loop 32. A similar path occurs where the cable 1 extends from the cross over point 31 on the femoral back plate 5 up to cable guides on either side of the femoral plate 4, connecting to the adjustment mechanism 6.

In additional embodiments of the present invention, the tibial plate may include additional portions which increase the hold on the wearer's tibia. Increased tibia control offers additional protection from hyperextension. As there is little tissue between the tibia and the external portion of the leg, this area is ideal for control of the leg. In some embodiments, the underside of the tibia plate, closest to the user's leg, may include an additional semi-ridged portion. As the cable system is tightened, for example, this semi-ridged portion conforms to the shape of the user's tibia. This provides an increased hold on the tibia.

In additional embodiments of the present invention, the tibia plate may be constructed such that the plate has varying flexibility across itself. For example, this varying flexibility would allow the tibia plate to conform to the shape of the user's leg, while also providing the necessary rigidity. In this example, a second semi-ridged portion may not be required, or, alternatively, may be offered in addition to the second semi-ridged portion.

In additional embodiments of the present invention, the user may, of course, use the brace as a preventative device, before any damage occurs, as opposed to after. In such a case, additional protection may be required. For example, user's engaged in extreme sports may require supplemental protection from impacts. Embodiments of the present invention may, therefore, include knee caps which protect the knee from strike forces. In some embodiments, the knee cap portion is disposed between the tibial and femoral plates such that when the plates pivot away from one another, the knee cap remains in place. In such an example, the tibial and femoral plates glide over or beneath the knee cap portion so as to allow necessary flexibility. Further, additional padding at the front of the knee may be added in order to both support the knee and protect it from strike forces.

While the invention has been described and illustrated with regard to the particular embodiment, changes and modifications may readily be made, and it is intended that the claims cover any changes, modifications, or adaptations that fall within the spirit and scope of the invention. Changes and modifications can readily be made to adapt this tibial shell Q angle adjustment invention to conventional knee braces. It is also anticipated that this invention can be adapted to an elbow brace by substituting the adjustable tibial shell with an adjustable radius shell. This allows a symmetrical elbow brace to be adjusted to fit the angle between the humerus and radius of the user's arm, and can be adjusted to fit a right or left arm.

The invention claimed is:

1. A knee brace comprising:

a femoral plate;

a first tibial plate hingedly coupled to the femoral plate and comprising first and second bearing surfaces, the first bearing surface being disposed on a first side of the first tibial plate, the second bearing surface being disposed on a second side of the first tibial plate opposing the first side;

a second tibial plate rotatable relative to the first tibial plate about an axis that intersects the first tibial plate and the second tibial plate while the second tibial plate is coupled to the first tibial plate, wherein the axis extends through a leg of a subject while the subject is wearing the knee brace;

first and second adjustment screws coupled to the second tibial plate, the first and second adjustment screws configured to respectively engage the first and second bearing surfaces of the first tibial plate, the first and second adjustment screws being configured to set an angle of rotation of the second tibial plate about the axis in response to manipulation of the first and second adjustment screws by a user of the knee brace;

a back plate; and a cable, the routing of the cable starting from the femoral plate extending downwardly toward the first tibial plate over a first anterior, distal surface of the femoral plate, continuing around the back plate, and further continuing around a first, anterior, distal surface of the first tibial plate and to and around a first, anterior, distal surface of the second tibial plate, the routing of the cable then continuing upwardly toward the femoral plate around a second, anterior, distal surface of the second tibial plate to a second anterior, distal surface of the first tibial plate, then continuing again around the back plate to cross with itself at a cross over point proximate a medial portion of the back plate, and the routing of the cable further continuing over a second anterior, distal surface of the femoral plate.

2. The knee brace of claim 1 wherein the angle of rotation comprises a Q-angle.

3. The knee brace of claim 1 wherein the femoral plate includes cable connectors.

4. The knee brace of claim 1 further comprising padding located underneath at least one of the femoral plate, first tibial plate, second tibial plate, or back plate.

5. The knee brace of claim 1 wherein the routing of the cable includes the is attached to one of the first tibial plate or the second tibial plate.

6. The knee brace of claim 1 further comprising a locking device coupled to the femoral plate and configured to secure the cable to the femoral plate.

7. The knee brace of claim 1 wherein the cable further comprises two segments, a femoral control loop and a tibial control loop, wherein the femoral control loop segment is formed by the portion of the cable from a cross-over point located on the back plate extending over the femoral plate and returning to the cross-over point, creating a loop configured to be around the user's leg, and further wherein the tibial control loop segment comprises the portion of cable extending from the cross-over point to at least the second tibial plate and returning to the cross-over point, creating a loop configured to be around the user's lower leg.

8. The knee brace of claim 1 wherein the routing of the cable includes a first adjustment mechanism located on the femoral plate, and further where selective engagement of the adjustment mechanism controls a length of the cable.

9. The knee brace of claim 1 wherein the cable includes two or more cable segments coupled together.

10. The knee brace of claim 1 further comprising wherein the routing of the cable further comprises two segments, a femoral control loop and a tibial control loop, wherein the femoral control loop segment is formed by a portion of the cable extending from the cross over point over the first anterior, distal surface of the femoral plate and down the second anterior distal surface of the femoral plate, returning to the cross over point, creating the femoral control loop to be configured to be around a user's leg, and further wherein the tibial control loop segment comprises the portion of cable extending from the cross over point to at least the first anterior distal surface of the second tibial plate and down the second anterior distal surface of the second tibial plate returning to the cross over point, creating the tibial control loop to be configured to be around a lower portion of the user's leg.

11. The knee brace of claim 10 further comprising where the lengths of the femoral control loop and the tibial control loop are directly inverse.

* * * * *